United States Patent [19]

Byrd

[11] Patent Number: 4,918,391
[45] Date of Patent: Apr. 17, 1990

[54] SODIUM CONTENT MONITOR HAVING A UNITARY HOUSING

[75] Inventor: Jeffrey M. Byrd, Pembroke Pines, Fla.

[73] Assignee: Enseal, Inc., Fort Lauderdale, Fla.

[21] Appl. No.: 169,434

[22] Filed: Mar. 17, 1988

[51] Int. Cl.⁴ ............................................. G01N 27/02
[52] U.S. Cl. .................................... 324/446; 324/444; 324/439; 204/400
[58] Field of Search ............... 324/438, 439, 444, 446, 324/450, 65 R, 99 D, 65 P, 149, 61 P; 204/1 T, 400, 407, 280

[56] References Cited

U.S. PATENT DOCUMENTS

| | | | |
|---|---|---|---|
| 3,302,102 | 1/1967 | Lace | 324/149 |
| 3,882,383 | 5/1975 | Matlin | 324/65 P X |
| 4,115,733 | 9/1978 | Silberberg | 324/99 D |
| 4,331,923 | 5/1982 | Akers, Jr. | 324/446 X |
| 4,753,247 | 6/1988 | Kirsner | 324/65 P |

OTHER PUBLICATIONS

"Food Anaylsis Lboratory Experiments" Second Edition by Clifton E. Meloan, Ph.D. and Yeshajahu Pomeranz, Ph.D. published by the AVI Publishing Company, Inc. Westport, Conn., May 19870 (Chapter 8–entitled Conductivity–Milk Adulteration and Household Disinfectants.

Primary Examiner—Reinhard J. Eisenzopf
Assistant Examiner—Jack B. Harvey
Attorney, Agent, or Firm—Richard M. Saccocio

[57] ABSTRACT

A salt sensor is disclosed which is portable and easily handled by a person at a restaurant or in his home for determining the sodium content of the food or beverage he is about to consume. The salt sensor includes a uniquely designed contact tip which is electronically connected to a circuit which generates an AC signal. The strength of the signal transmitted across the contact tips is directly proportional to the conductivity of the food or beverage being tested and is, accordingly, registered on a display panel located on the body of the salt sensor.

7 Claims, 3 Drawing Sheets

SODIUM CONTENT MONITOR HAVING A UNITARY HOUSING

BACKGROUND OF THE INVENTION

1. Field of the Invention

This invention relates in general to the field of electronic testing apparatus and in particular to a portable hand-held electronically-operated sensor which may be used to determine the sodium content of foods.

2. Description of the Prior Art

Sodium has been directly linked to causing high blood pressure, heart disease and other cardio-vascular disorders. The public has become more aware of the possible detrimental effects of sodium and is showing signs of concern. In partial response thereto certain manufacturers have introduced food products containing less sodium. Other manufacturers have even listed the sodium content per serving on the containers within which the food is packaged. However, these efforts, while laudatory, are not sufficient in and of themselves. Notwithstanding these efforts, for example, a person rarely knows how much sodium intake he is receiving as a result of the foods he is eating, or as a result of the liquids he is consuming.

Since ordinary salt contributes more than eighty percent (80%) of the sodium intake of Americans, avoiding salt alone can considerably reduce the sodium intake of people. Avoiding the intentional use of salt on foods also does not solve the problem. There are very high levels of salt in many of the foods within a person's diet which levels go unnoticed or undetected by the people. The use of taste buds to detect salt within food is not a reliable method. Taste buds can be very easily fooled by other chemicals or ingredients found in the food or can become accustomed to salt so that its presence would not be detected.

Accordingly, an object of the present invention is to provide apparatus which can be used by a person at the time he is eating or drinking, which apparatus can be used to measure the level of the sodium in the food and drink he is consuming.

The above-stated objects as well as other objects which although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The present invention accomplishes the above-stated objectives as well as others by providing a hand-held and easily operable salt sensor.

The salt sensor has a housing which includes a handle portion and a sensing tip. A switch at the handle end activates an electronic circuit contained with the body of the housing which circuit, in conjunction with the sensing tip, registers the amount of sodium per ounce on a display panel located on the handle portion. Thus, in operation, the tip of the probe is placed in the food to be tested and then the switch is activated. While the probe is still immersed within the food, a reading will appear on the display panel of the device. To discontinue testing of the sodium content in the food, the switch is deactivated and the probe is removed from the food. By simply wiping off the tip of the probe, the device is ready for subsequent testing. By using this simple procedure, a person can determine the sodium content per ounce of each of the foods and/or liquids he is about ready to consume during a meal or snack.

The electronic circuit within the probe includes a 1,000 Hz generator connected to one contact of a stainless steel sensor which is located on the outside tip of the device. The other contact of the sensor is connected to an AC amplifier, an AC-DC converter and a circuit containing a plurality of parallel-arranged LEDs. The LEDs are electronically arranged such that current passing between the contacts of the sensing tip corresponds to only one of the plurality of LEDs, causing that LED to light up and thereby indicate the amount of sodium per ounce of the food being tested.

In an alternative embodiment the AC-DC converter is connected to an analog-to-digital converter which is connected to a digital display panel. The digital display panel indicates in numerically the amount of sodium per ounce of the food tested.

DESCRIPTION OF THE DRAWINGS

Various other objects, advantages and features of the invention will become apparent to those skilled in the art from the following discussion taken in conjunction with the following drawings, in which.

DESCRIPTION OF THE PREFERRED EMBODIMENTS

Figures 1, 2, 4:
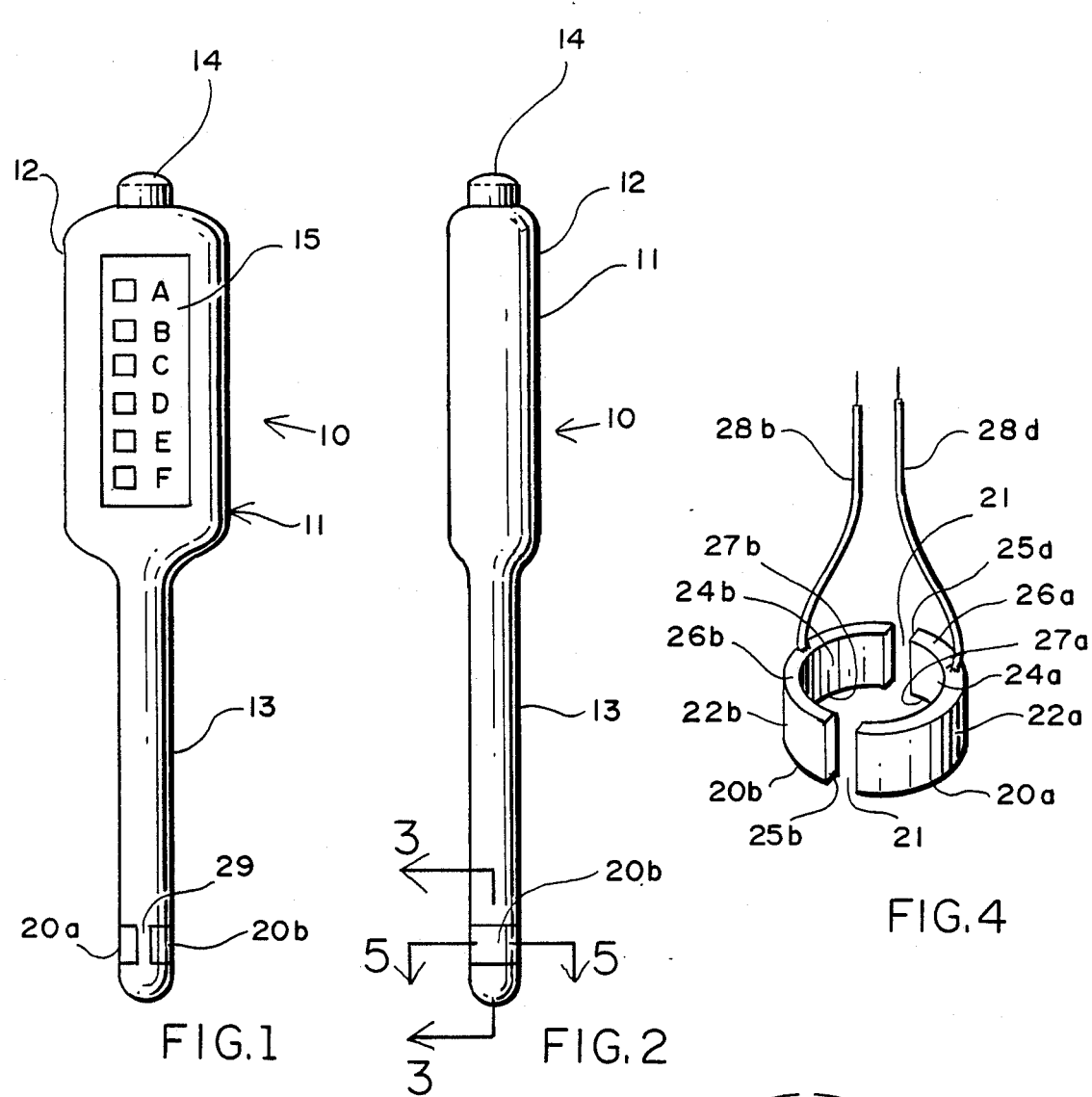
FIG. 1 is a front elevational plan view of the housing of the inventive salt sensor.
FIG. 2 is a side elevational plan view of the housing of the inventive salt sensor.
FIG. 4 is an isometric view of th sensing contact tip of the salt sensor.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings wherein like characteristics and features of the present invention shown in the various figures are designated by the same reference numerals.

The overall shape and configuration of the inventive salt sensor is shown in FIGS. 1 and 2. Salt sensor 10 includes a housing 11 which is relatively flat and end thin in a side view and is somewhat broader in a frontal view. Housing 11 includes an upper portion 12 and a lower portion 13. Upper portion 14 contains the electronics necessary to allow the salt sensor to function as more fully explained hereinafter. Upper portion 11 is the portion which is normally held or handled by the person using the device. Accordingly, while its overall shape is relatively immaterial, it should be such that it can easily fit within the palm of a person's hand and not have any obstructions thereon which might interfere with the proper handling of the device.

The lower portion 13 comprises the sensing probe portion of the device. This is the portion that is actually placed within the food for which the sodium content is to be determined. Accordingly, its shape should be relatively thin and elongated with the tip portion being rounded or slightly pointed so that it may readily be inserted within the food to be tested.

The overall length of the salt sensor 10 may be approximately five-to-seven inches. The diameter of the sensing probe portion 13 may be of the order of one-quarter of an inch. The side sectional width may be of the order of three-eights to one-half inch while the frontal side width may of the order of one inch. The salt sensor 10 having these approximate dimensions may easily be carried by a person in one of his pockets to a location such as a restaurant or even within his home where the food to be consumed is to be tested.

At the top of the upper portion 11, there is provided a switch 14 which after the inventive device 10 is inserted within the food to be tested, is pressed to activate the circuitry therewithin. The circuitry then measures the sodium content per ounce of the food being tested, and registers the amount of sodium per unit volume of the food on the display panel 15 located on the upper portion 12 of the inventive salt sensor 10. Once the sodium content has been registered and duly noted by the person using the same, switch 14 may be deactivated and the probe withdrawn from the food for use with another food. At this point in time, the probe tip 13 should be wiped clean with a paper or cloth napkin or other appropriate means in order to both clean the probe tip as well as prevent any food remaining thereon from altering the true reading of the next food to be tested.

Figures 3, 5:
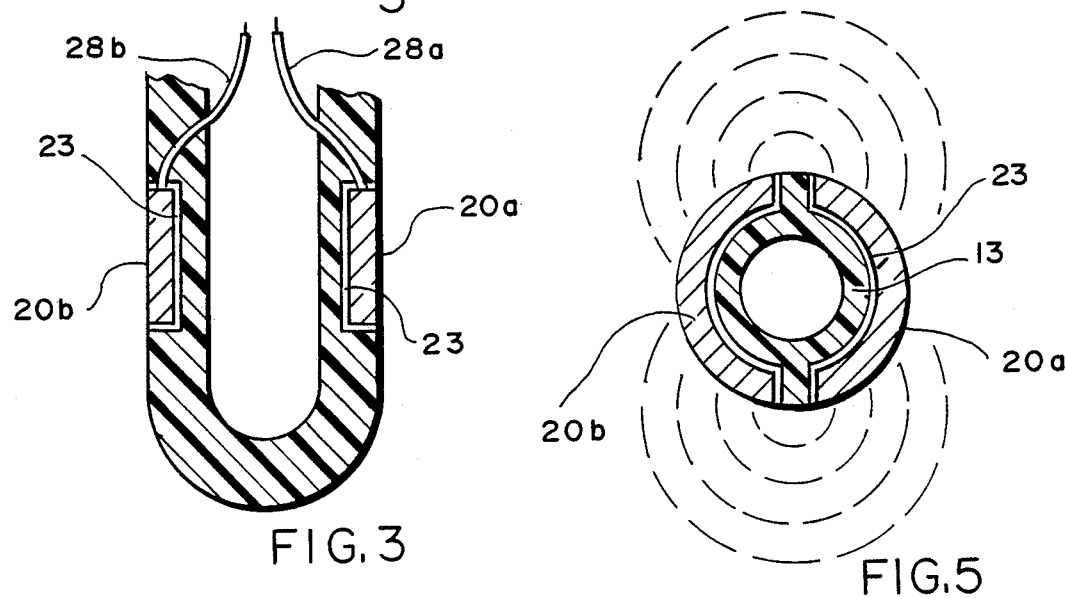
FIG. 3 is a cross-sectional view of the tip of the salt sensor of FIG. 2, taken through the line 3—3 thereof.
FIG. 5 is a schematic illustration of the current path of the two halves of the sensing tip.

FIG. 3 is an enlarged cross-sectional view of the lower portion 13 of the salt sensor 10. In FIG. 3 the manner of arranging the contacts 20 of the sensor is shown. The contacts 20 are further shown in FIG. 4 with the bottom portion 13 of the sensing probe being removed for purposes of clarity.

Referring now also to FIGS. 3 and 4, it is seen that the contact 20 includes a first contact 20a and a second contact 20b. Each of which comprises a thin strip of a metal such as stainless steel which is bent in a semi-circular configuration. When the contacts 20a and 20b are assembled to the tip of the probe 13, a small gap 21 is formed between each end of contacts 20a and 20b.

The outside surface 22 of contacts 20, when assembled to the probe tip 13, is flush with the outer surface of the probe tip 13. This arrangement is provided so that no crevices or steps exist on the tip 13 of probe 10. A step or crevice will cause food to be lodged therein, which food can alter the true reading of the sodium content of the food being tested. A liner material 23 is provided between the inside surface 24, the side surfaces 25, the top surfaces 26, and the bottom surfaces 27 of the contacts 20. Liner 23 comprises an insulator which serves to insulate surfaces 22, 23, 24, 25, and 26.

In this manner when the inventive salt sensor 10 is being used to measure the sodium content of a food, the current flowing through contacts 20a and 20b can only flow from the outside surface 22 of contact 20a to the other outside surface 22 of contact 20b and vice versa. Any current flow between any surfaces other than surfaces 22a and 22b would alter the true reading of the sodium content in the food to be tested.

As schematically shown in FIG. 4, a first electrical lead 28a is attached to contact 22a while a second electrical lead 28b is attached to contact 22b. Electrical leads 28a and 28b serve, of course, to conduct current to the contacts 22a and 22b and to conduct current from the contacts 22a and 22b when the circuit within the inventive salt sensor 10 is completed by pressing switch 14.

The liner 23 serves to prevent current from flowing from side surfaces 25a of contact 22a to side surfaces 25b of contact 22b. In addition, the material from which the probe portion 13 of the salt sensor is made is caused to be located between side surfaces of the contacts 22a and 22b. In other words the material from which the housing is made is also within the gap 21 between the contact portions 22a and 22b. Again, a flush fit is effectuated. This means that the surfaces 29 of the small portion of the probe portion 13 which fits within gaps 21 are flush with surfaces 22a and 22b of contacts 20a and 20b, respectively. In this manner no gaps or crevices or steps exist between the surface of probe portion 13 and any surface of the contacts 20a and 20b.

FIG. 5 shows the cross-sectional configuration of the probe portion 13 at the location of contacts 20a and 20b. In FIG. 5 it is seen how liner 23 fully insulates the inside surfaces of contacts 20a from the probe material. Liner 23 serves a further function of preventing a liquid from the food or beverage to be tested from getting in between the inside surfaces 24, 25, 26, and 27 of contacts 20. Any liquid communication from these surfaces between contacts 20a and 20b would render the reading provided by the salt sensor 10 to be incorrect. Accordingly, liner 23 serves an insulating function such that the current flowing between contacts 20a and 20b is as schematically shown in FIG. 5. That is, that the flow of electricity is only from the outside surface 22a to the other outside surface 22b of contacts 20a and 20b.

Figure 6:
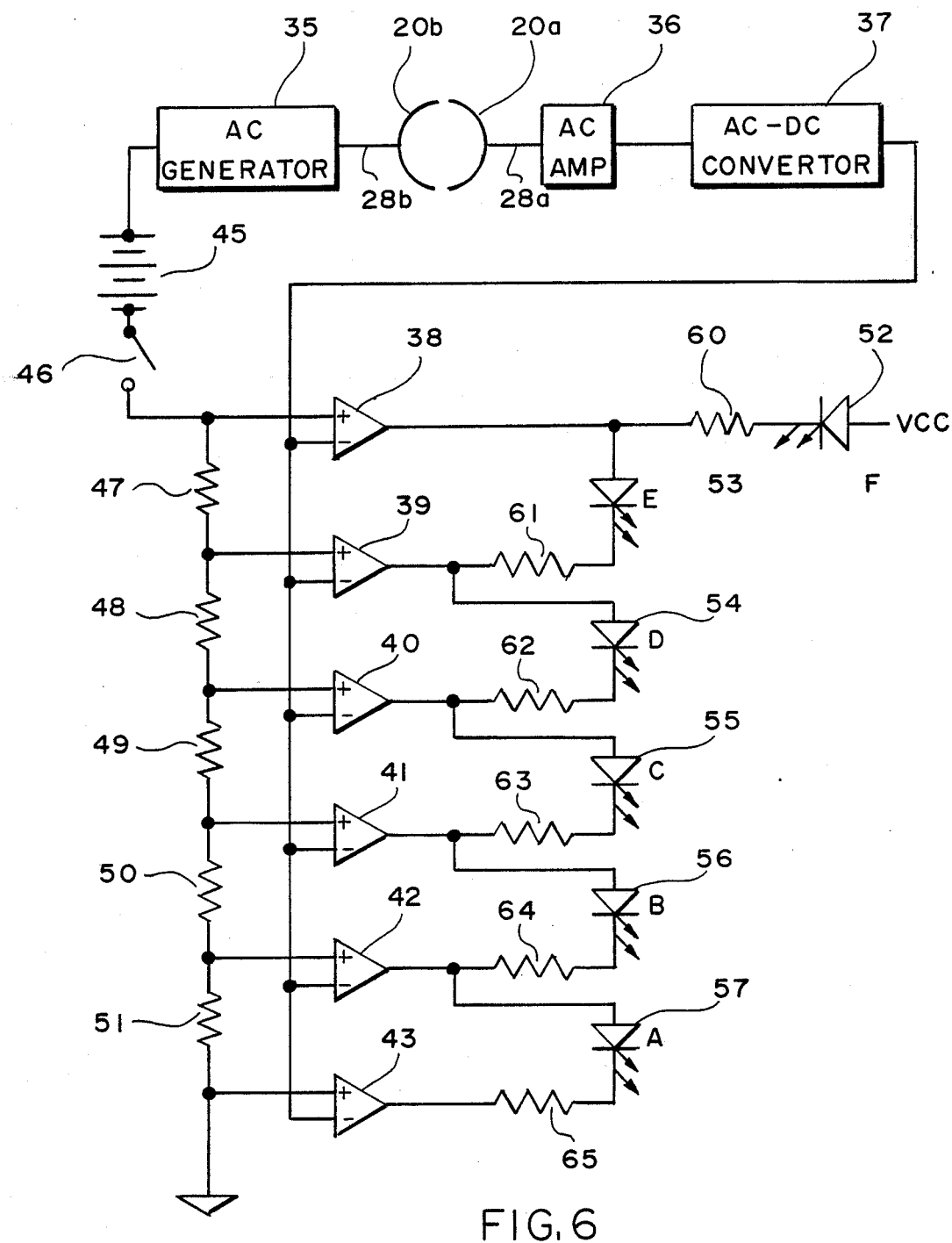
FIG. 6 is a schematic electrical diagram illustrating the circuitry used within the body of the salt sensor to measure the amount of sodium within a food or a beverage; and, FIG. 6A is a schematic electrical diagram illustrating the circuitry used to measure and numerically display the amount of sodium in a food or beverage being tested.

The electrical circuit of the salt sensor 10 is shown in FIG. 6. A signal generator 35 which is capable of producing a 1,000 Hz signal, is connected on one side to a DC voltage source and the other side to one of the electrical leads, such as 28a, leading to the contact 20. Leading from contact 20b is lead 28b which is input to an AC amplifier which is used to amplify the AC signal being transmitted across contacts 20a and 20b. The amplified signal is then transmitted to AC-to-DC converter 37. Converter 37 is required because the signal generated by generator 35 is an alternating current circuit which, for example, may vary between $+1\frac{1}{2}$ volts to $-1\frac{1}{2}$ volts and may comprise a square wave signal.

An AC signal is preferred across contacts 20a and 20b because it eliminates any hydrolysis effect which may occur when the contacts 20a and 20b are immersed within the food or beverage to be tested. Were a DC signal to be transmitted across contacts 28a and 20b, the same would cause hydrolysis of the food or beverage being tested and would result in contaminants from the hydrolysis being deposited on one of the two contacts 20a or 20b. Moreover, such contamination could not merely be wiped off. It would be an electrical deposition of the contaminating material. The use of an AC signal completely eliminates this undesirable effect. The AC signal continuously varies in direction across contacts 20a and 20b. Tests have shown that such an alternating current signal either prevents hydrolysis or eliminates its effect. In either event there is no deposition of any contaminating material on either of the contacts 20a or 20b. Thus, the inventive salt sensing device 10 may be used time and time again without altering the calibration of the strength of the electrical signal relative to the sodium content which is initially designed within the salt sensor 10.

The signal from the AC-to-DC converter 37 is transmitted to the plurality of parallel arranged comparators 38, 39, 40, 41, 42, and 43. This signal is, for example, sent to the negative leg of comparators 39 through 43. The positive leg of comparators 39 through 43 is provided with a signal directly from the voltage source 45 when switch 46 is closed.

In the manner shown in FIG. 6 of the drawings the electrical signal from voltage source 45 is a maximum to comparator 38. Since the voltage signal sent to comparator 39 must first pass through resistor 47, its value will be less than signals sent to comparator 38. Similarly, the signal sent to comparator 39 is greater than that sent to comparator 40 and so on, such that the signal to comparator 41 is greater than that sent to comparator 40, and the signal sent to comparator 41 is greater than that sent to comparator 42, and the signal sent to comparator 42 is greater than that sent to comparator 43. The continually decreasing signal sent to the comparators 38 through 43 results from the signal continuously being reduced by resistors 47, 48, 49, 50, and 51.

Each of comparators 38 through 43 compare the signal sent to its negative leg with respect to the signal sent to its positive leg. Only if the two are the same does one of the comparators send a positive signal through one of the LEDs 53 through 57. LEDs 53-57 are electrically connected to the comparators 38 through 43 as shown in FIG. 6 of the drawings.

For example, should the signal be such that comparator 40 determines that the signal from its positive and the signal from its negative legs are the same, then it would register such a condition and send a signal to one leg of LED 55. A positive signal would also be sent to one leg of LED 54. However, because of resistor 62, this signal will be virtually zero. Since no signal will be sent from comparator 39 to the other leg of LED 54, LED 54 will not light up. Since comparator 41 will compare the signals and determine that they are not similar, comparator 41 will not send a signal to the other leg of LED 55. Since LED 55 has a signal differential thereacross, LED 55 will light up. Similarly, LEDs 53, 56, and 57 will also not light up along with LED 54. That LED 55 is the only one lighted is as previously stated a function of the strength of the signal transmitted by the 1000 Hz generator across contacts 20 through an AC amp 36, through an AC-to-DC convertor 37, and then to each of the comparators 38 through 43. The strength of the signal is directly related to the conductivity of the food being tested as sensed by contacts 20a and 20b. LEDs 53 through 57 may be arranged to each light up, depending upon the conductivity of the food or beverage being tested for sodium content. The calibration designed within the electrical circuit of salt sensor 10 may be such that, for example, LED 57 corresponds to ten milligrams per ounce, LED 56 corresponds to twenty milligrams per ounce, LED 55 corresponds to thirty milligrams per ounce, LED 54 corresponds to forty milligrams per ounce, and LED 53 corresponds to fifty milligrams or more per ounce of sodium of the food or beverage being tested. Of course, other calibrated figures may be designed into the unit consistent with the overall range of the expected sodium content of food or beverages.

In accordance with the above there has been disclosed and explained a portable salt sensor which may be conveniently used by a person to test the sodium content of the food or beverage he is about to consume.

Figures 1A, 6A:
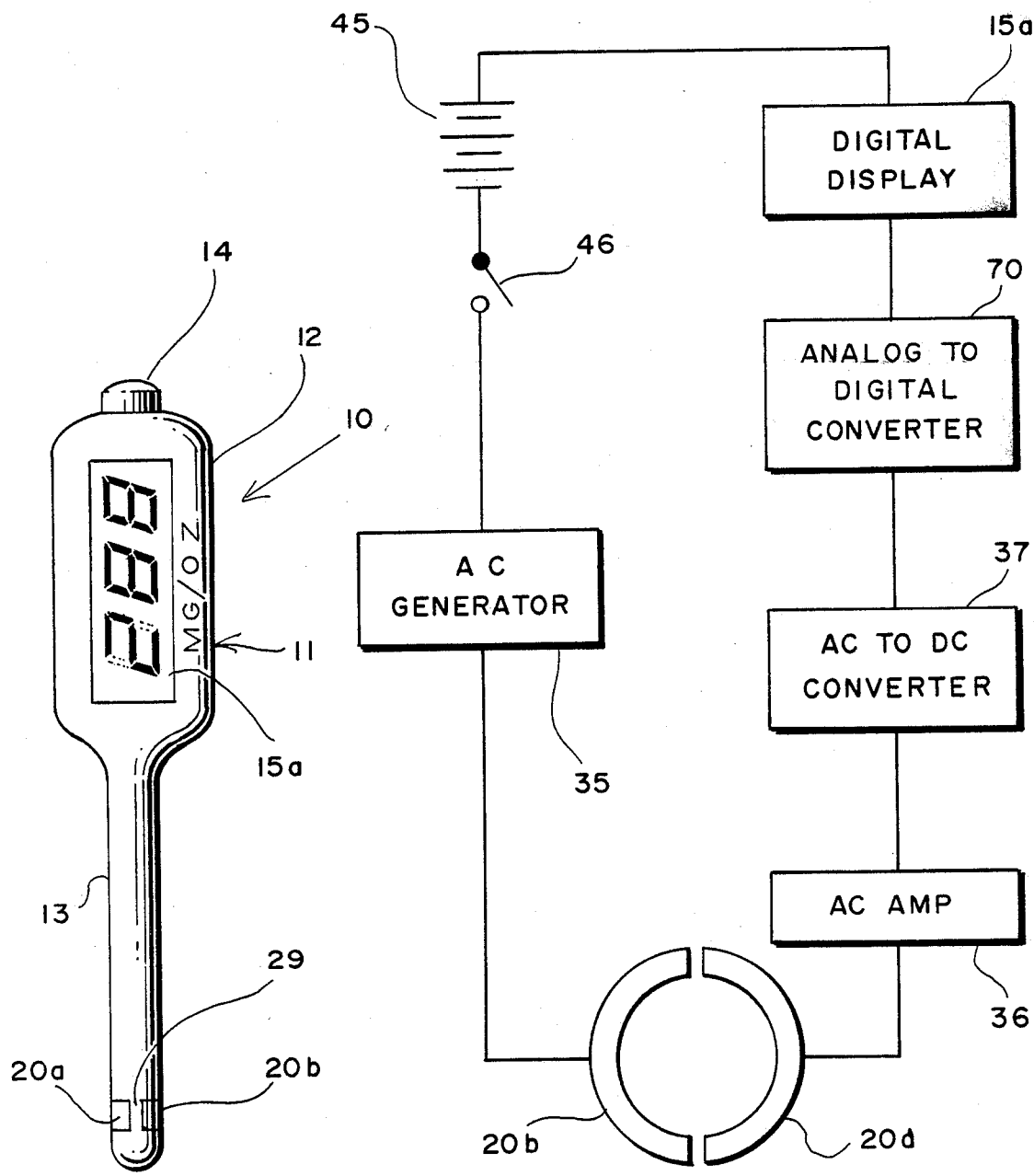
FIG. 1A is a front elevational plan view of the housing of an alternative embodiment of the inventive salt sensor.

The housing and electrical schematic drawing of an alternate embodiment are shown in FIGS. 1a and 6a. In the alternative embodiment the amount of sodium per ounce of food or beverage being tested is registered and displayed in digital or numerical form on the display panel 15a of the upper portion 12 of the housing 11. The display panel 15a may utilize LEDs or LCDs to indicate the numerical value of the sodium in milligrams per ounce.

An analog to digital converter 70 converts the signal from the AC-DC converter 37 from an analog signal to a digital signal. The digital signal is input to the digital display panel 15a which directly displays the amount of sodium in the food or beverage being tested. As shown in FIG. 6a, the remaining components and arrangement thereof are similar to the embodiment of FIG. 6.

While the invention has been described, disclosed, illustrated and shown in certain terms or certain embodiments or modifications which is has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

I claim as my invention:

1. Apparatus for measuring the sodium content of foods or beverages comprising a unitary housing including a body portion and a probe portion, said body portion containing an electronic circuit for operating the apparatus, said probe portion having sensing contacts attached to an end thereof a liner member between said contacts and said probe portion whereby a substantially crevice-free arrangement is created between said contacts and said probe a switch attached to said housing for activating said electronic circuit said electronic circuit comprising an AC generator, an AC amplifier, an AC-DC convertor, and means for converting a signal from the AC-DC converter into a visual signal which is displayed on said housing.

2. The apparatus of claim 1, wherein said visually displayed signal comprises a plurality of LEDs, said LEDs being sequentially arranged to indicate in ascending order the amount of sodium per unit volume in the food or beverage being tested.

3. The apparatus of claim 1, wherein said visually displayed signal comprises a direct reading digital number.

4. The apparatus of claim 1, wherein said sensing contacts comprise two strips of metal with a space therebetween, each strip being electrically attached to said electronic circuit.

5. The apparatus of claim 4, wherein said sensing contacts each comprise a curved strip of metal assembled with the concave surface of each facing each other and said space therebetween comprises the space between adjacent ends of said strips of metal.

6. The apparatus of claim 5, wherein said curved sensing strips are each fitted into a cutout in the probe portion of the housing around the periphery thereof.

7. The apparatus of claim 6, wherein the outside convex surfaces of said curved strips fit flush with the outside periphery of said probe portion.

* * * * *